(12) United States Patent
Sakai et al.

(10) Patent No.: US 8,599,379 B2
(45) Date of Patent: Dec. 3, 2013

(54) METHOD FOR INSPECTING DEFECTS AND DEFECT INSPECTING APPARATUS

(75) Inventors: Kazufumi Sakai, Saga (JP); Kazuhiro Nonaka, Saga (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 383 days.

(21) Appl. No.: 12/993,389

(22) PCT Filed: May 22, 2009

(86) PCT No.: PCT/JP2009/059460
§ 371 (c)(1),
(2), (4) Date: Nov. 18, 2010

(87) PCT Pub. No.: WO2009/142305
PCT Pub. Date: Nov. 26, 2009

(65) Prior Publication Data
US 2011/0069313 A1    Mar. 24, 2011

(30) Foreign Application Priority Data

May 22, 2008 (JP) ................................. 2008-133809

(51) Int. Cl.
*G01J 4/00* (2006.01)
*G01N 21/00* (2006.01)

(52) U.S. Cl.
USPC ........................... 356/369; 356/237.1

(58) Field of Classification Search
None
See application file for complete search history.

(56) References Cited

U.S. PATENT DOCUMENTS 5,424,536 A * 6/1995 Moriya ......................... 250/225
5,936,726 A * 8/1999 Takeda et al. ............... 356/237.2
6,124,926 A 9/2000 Ogawa et al.
6,285,449 B1 * 9/2001 Ellingson et al. .......... 356/237.1

(Continued)

FOREIGN PATENT DOCUMENTS

JP    62-177447 A    8/1987
JP    4-118540 A     4/1992

(Continued)

OTHER PUBLICATIONS

International Search Report of PCT/JP2009/059460, mailing date Jun. 30, 2009.

*Primary Examiner* — Gordon Stock, Jr.
(74) *Attorney, Agent, or Firm* — Westerman, Hattori, Daniels & Adrian, LLP

(57) ABSTRACT

Light from a light source device (4) is polarized through a polarizer (5) and is caused to impinge obliquely on an object (W) to be inspected. The resulting scattered light (SB) is received by a CCD imaging device (7) having an element (9) for separating scattered light disposed in a dark field. Component light intensities are worked out for an obtained P-polarized component image and an obtained S-polarized component image and a polarization direction is determined as a ratio of them. The component light intensities and the polarization directions are determined from images obtained by imaging of the light scattering entities in a state where stress is applied to the object to be inspected and in a state where stress is not applied thereto. The component light intensities and the polarization directions are compared with predetermined threshold values. As a result, defects in the inspection object, such as internal deposits or cavity defects, foreign matter or scratches on the surface or cracks in the surface layer can be detected with high precision and the defects can be classified by identifying the type of the defect.

13 Claims, 9 Drawing Sheets

(56) References Cited

U.S. PATENT DOCUMENTS

| | | |
|---|---|---|
| 6,449,037 B2 * | 9/2002 | Jun et al. .................... 356/237.4 |
| 6,726,319 B1 | 4/2004 | Yanase et al. |
| 6,731,384 B2 | 5/2004 | Ohshima et al. |
| 7,684,032 B1 * | 3/2010 | Meeks .................... 356/237.2 |
| 2012/0007978 A1 * | 1/2012 | Passek et al. .................... 348/87 |
| 2012/0262715 A1 * | 10/2012 | Sakai et al. .................... 356/369 |

FOREIGN PATENT DOCUMENTS

| | | | |
|---|---|---|---|
| JP | 4128664 | A | 4/1992 |
| JP | 5-018889 | A | 1/1993 |
| JP | 6-281589 | A | 10/1994 |
| JP | 7-318500 | A | 12/1995 |
| JP | 10-293102 | A | 11/1998 |
| JP | 10-293103 | A | 11/1998 |
| JP | 11-211668 | A | 8/1999 |
| JP | 2000-216208 | A | 8/2000 |
| JP | 2001-208729 | A | 8/2001 |
| JP | 2002-188999 | A | 7/2002 |
| JP | 2005-093968 | A | 4/2005 |
| JP | 2005-147813 | A | 6/2005 |
| JP | 3664134 | B2 | 6/2005 |
| JP | 2008-008740 | A | 1/2008 |

* cited by examiner

SCATTERED LIGHT SPOT

METHOD FOR INSPECTING DEFECTS AND DEFECT INSPECTING APPARATUS

FIELD OF THE INVENTION

The present invention relates to a method for inspecting defects in an object to be inspected and to a defect inspecting apparatus. More particularly, the present invention relates to a method for inspecting defects and a defect inspecting apparatus for detection and/or classification of defects in an object to be inspected, for which a high degree of homogeneity is required, such as a semiconductor wafer.

BACKGROUND OF THE INVENTION

In semiconductor manufacturing processes, the presence of defects inside wafers causes deterioration or impairment of electric characteristics in a semiconductor device as a manufactured article. In manufacturing semiconductor devices, therefore, wafers are inspected for defects at a stage before semiconductor manufacturing or after being subjected to a surface treatment during the manufacturing process. When a wafer having defects is processed as-is, the final semiconductor article becomes a defective one. Therefore, defects must be eliminated beforehand.

Recent years have witnessed ever higher degrees of integration in semiconductor devices and ever finer patterns in the devices and thus the size of wafer defects to be inspected has become smaller. The need for higher defect detection power has increased accordingly. Defect detection includes destructive methods and non-destructive methods. In the former, the wafer is dissolved in an etching solution or is physically abraded to expose, on the surface, defects that are then observed with a microscope or an electron microscope. However, wafers inspected in accordance with the above methods can no longer be used for semiconductor device manufacturing.

Non-destructive inspection methods include electric methods and contact-less inspection methods that utilize light or ultrasonic waves. In electric inspection methods, electrodes are attached to the wafer or probes are made to contact with the wafer. Electric signals are then applied to the wafer and the presence of defects in the wafer is detected on the basis of changes in the electric signals. However, it is difficult to pinpoint thereby the position of the defects. Also, contact with electrodes or the like is required. Such methods cannot be used thus at the manufacturing stage of the article.

In defect detection by ultrasonic waves, ultrasonic waves are applied onto the object to be inspected and the ultrasonic waves reflected by defects are detected by a detector. Internal defects in a material through which light cannot pass, such as metals or the like, can be detected and hence the method is used, for instance, for inspecting package interiors. In terms of detection limits and resolving power, however, the method cannot be used for detecting wafer defects and foreign matter with high resolution.

In inspection methods that utilize light, light scattered by defects or foreign matter is detected by a optical system placed in dark-field or bright-field and position of defect is detected at the same time. For detecting defects inside wafers, lasers, for which silicon is transparent, are used, while visible-light lasers are used for detecting defects in the surface or surface layers.

Defect inspection schemes that utilize light or ultrasonic waves are disclosed in prior art documents such as the following.

Japan Patent Application Laid-open JP, S62-177447, A (Patent Document 1) discloses an ultrasonic damage inspection method for objects to be inspected such as piping or steel, wherein electromagnetic ultrasonic waves are transmitted to the object to be inspected, a laser beam is aimed at the portion of the object to be inspected that is excited by the ultrasonic waves and defects in the object to be inspected, plate thickness and the like are detected on the basis of resulting reflected signals.

Japan Patent Application Laid-open JP, 2001-208729, A (Patent Document 2) discloses a defect detection device for detecting defects, wherein surface elastic waves from an ultrasonic vibrator impinge on an object to be inspected, a laser beam is irradiated onto the surface of the object to be inspected, the resulting reflected light is received, the frequency difference between the laser output light and the reflected light is detected by a signal processing device and vibration speed in the object to be inspected is measured on the basis of that difference.

Japan Patent Application Laid-open JP, 2005-147813, A (Patent Document 3) discloses a method and device for non-destructive inspection of a material, wherein internal defects of an object to be measured are detected by irradiating a pulsed laser beam onto the surface of the object to be measured, to generate elastic waves thereby; irradiating a continuous-emission laser beam for signals, coaxially with the pulsed laser, onto the surface of the object to be measured; and causing reflected light, influenced by the elastic waves and the scattering surface of the object to be measured, to impinge on a laser interferometer, whereby changes in a frequency component are detected.

Japan Patent Application Laid-open JP, 2002-188999, A (Patent Document 4) discloses that a laser beam is irradiated onto an object to be inspected such as a semiconductor wafer or the like; reflected and scattered light from the object to be inspected is detected in a plurality of directions; and the directionality of the reflected and scattered light is detected through comparison of the detection results, thereby foreign matter and defects, such as flaws or the like, in the object to be inspected being detected as well as distinguished therebetween.

Japan Patent Application Laid-open JP, H11-211668, A (Patent Document 5) discloses a defect inspection method wherein a laser beam impinges on a sample to be inspected, the resulting scattered light and the emission light are split into components with a plurality of dissimilar wavelength bands and form images on an imaging device and the nature of the defects is identified on the basis of the obtained plurality of images.

Japan Patent Application Laid-open JP, 2000-216208, A (Patent Document 6) discloses an inspection method in which two pulsed-emission laser beams, set to be at dissimilar incidence angles and have emission timings offset from each other, are irradiated onto the surface of a semiconductor wafer or the like, one of the laser beams being set so as to give rise to scattered light from both particles and pits and the other laser beam being set so that there is less scattered light from pits, wherein particles are distinguished from pits on the basis of the detection results from both types of scattered light.

In the defect inspection methods disclosed in Japan Patent Application Laid-open JP, H10-293101, A (Patent Documents 7) and Japan Patent Application Laid-open JP, H10-293102, A (Patent Document 8), a wavelength $\lambda 1$ at which reflectance R takes a maximum value and a wavelength $\lambda 2$ at which reflectance R takes a minimum value, upon a change of the wavelength of a laser beam that impinges on an object to be inspected, are determined beforehand and optical information is obtained at the time at which laser beams of wavelengths λ1, λ2 impinge on the object to be inspected, whereby surface defects are distinguished from defects very near the surface layer of the object to be inspected. Also in this, the laser beams impinge obliquely on the object to be inspected and a total image which shows scattering by defects can be observed in a microscope that is disposed above the object to be inspected.

Japan Patent JP, 3664134, B (Patent Document 9) discloses a method for inspecting a semiconductor wafer surface, wherein a laser beam is irradiated onto and scanned over a wafer surface; light reflected or scattered by the wafer surface is received by a plurality of light-receiving systems having dissimilar light-receiving angles (high angle, low angle) with respect to incident light; and differences between standard reduced particle sizes on the basis of ratios of the light intensities received by the plurality of light-receiving systems are obtained, so as to determine the character and type of the defects.

Japan Patent Application Laid-open JP, 2008-8740, A (Patent Document 10) by the present inventors discloses a method and apparatus in which a laser beam is irradiated onto a wafer surface in a state where ultrasonic waves are being applied onto the wafer and in a state where ultrasonic waves are not applied and the change of intensity of light scattered by cavity defects, from before to after application of ultrasonic waves, is detected by a light-receiving means disposed in a cross-Nicol arrangement with respect to a polarizer, so that foreign matter is determined on the basis of changes in the intensities of the scattered light.

In Patent Documents 1 and 2, internal cavity defects cannot be detected with high resolution. In Patent Document 3, the presence or absence of internal defects can be detected but the influence on a scattering surface of the material surface, caused by ultrasonic waves, is detected in the form of signal light. This is appropriate for non-destructive inspection of concrete structures but not for high-resolution inspection of internal defects in semiconductor wafers or the like.

In Patent Documents 4 and 5, the nature of defects is identified on the basis of a relationship between directionalities of reflected or scattered light and wavelength bands. This approach, however, is not appropriate for high-precision detection of internal defects. In Patent Document 6, two pulsed laser beams are irradiated at timings offset from each other, hence the composition and control mechanisms involved are complex. Also, although surface defects such as particles and pits can be detected thereby, the method is not appropriate for detecting internal cavity defects.

In Patent Documents 7 and 8, surface defects and internal defects are distinguished on the basis of wavelength differences. However, it is not possible to determine whether the defects are internal cavity defects or not.

In Patent Document 9, the type and character of wafer surface defects are determined according to a combination of numerical values of standard reduced particle size of scattering elements, on the basis of scattered light intensity ratios at dissimilar light-receiving angles. However, cavity defects inside the wafer cannot be determined thereby.

In case of detecting foreign matter on a surface layer with the method disclosed in Patent Document 10, surface shift caused by ultrasonic waves may give rise to changes in scattering intensity, which in turn may result in misdetection. Also, only P-polarized or S-polarized light is detected, hence defects cannot be classified with sufficient certainty, which is problematic.

SUMMARY OF THE INVENTION

In inspecting an object to be inspected, such as a semiconductor wafer or the like for defects, cracks or the like in a surface layer could not be detected through conventional electric inspection or through defect inspection using light or stress, as described above. In an object to be inspected such as a semiconductor wafer, the method of removing a defect and the realizability for repair vary depending on the type of the defect. Therefore, it is necessary not only to determine the presence of defects in the object to be inspected but also to determine types of defects. There has been thus a demand for defect inspection that should allow detecting defects with high resolution and classifying the defects by distinguishing between defects such as foreign matter on the surface of the object to be inspected, cracks in the surface layer and internal deposits.

The present invention has been attained, pursuing to solve the above problems. The method of inspecting defects in an object to be inspected according to the present invention is a method for inspecting defects in an object to be inspected by polarizing, with a polarizer, light of a wavelength that can penetrate into the object to be inspected and irradiating the polarized light onto a surface of the object to be inspected, thereby detecting scattered light therefrom in a state where stress is not applied to the object to be inspected and in a state where stress is applied thereto, the method comprising: irradiating polarized light obliquely onto the surface of the object to be inspected, at a position thereof, in a state where stress is not applied to the object to be inspected and separating scattered light generated as a result of the irradiation into P-polarized component light and S-polarized component light, then obtaining intensities of each component light and a polarization direction as a ratio thereof; irradiating polarized light obliquely onto the surface of the object to be inspected, in a state where stress is applied to the object to be inspected, at the same position of the surface as where the light was irradiated in a state where no stress is applied to the object to be inspected and separating scattered light generated as a result of the irradiation into P-polarized component light and S-polarized component light, then obtaining intensities of each component light and a polarization direction as a ratio thereof; and detecting defects and/or classifying the defects by comparing the intensity and polarization direction of each component light obtained in a state where no stress is applied to the object to be inspected and the intensity and polarization direction of each component light obtained in a state where stress is applied to the object to be inspected respectively with a predetermined threshold value.

In another aspect, scattered light from light irradiated at the position on the surface of the object to be inspected is separated, by means for separating polarized light disposed in a dark field, into a P-polarized polarization component and an S-polarized polarization component so as to obtain the intensity of each component light.

In still another aspect, a defect in the object to be inspected is determined to be a crack or a cavity defect when a difference between the polarization direction of scattered light obtained in a state where no stress is applied to the object to be inspected and the polarization direction of scattered light obtained in a state where stress is applied to the object to be inspected exceeds a predetermined threshold value and a defect in the object to be inspected is determined to be another type of defect when the difference does not exceed the predetermined threshold value.

In still another aspect, the object to be inspected is disposed on a vacuum chuck with a piezoelectric element interposed therebetween and stress is applied to the object to be inspected through a suctioning action exerted by the vacuum chuck on the object to be inspected and through an action exerted by the piezoelectric element.

In still another aspect, the object to be inspected is heated and/or cooled so as to generate thermal stress in a state where the object to be inspected is disposed on a heating stage, whereby the object to be inspected is subjected to stress.

In still another aspect, the object to be inspected is subjected to stress through the action of ultrasonic waves on the object to be inspected.

In still another aspect, the object to be inspected is a silicon wafer for manufacturing semiconductor devices and an internal cavity defect is detected using infrared light as the irradiated light.

The defect inspecting apparatus according to the invention is a defect inspecting apparatus comprising: a support portion for supporting an object to be inspected placed thereon; stress applying means for applying stress to the object to be inspected that is capable of switching between a state in which stress is applied to the object to be inspected placed on the support portion and a state in which no stress is applied; a light source device that irradiates light with a wavelength that can penetrate into the object to be inspected via a polarizer obliquely onto a surface of the object to be inspected supported by the support portion; a scanning driving unit that causes the object to be inspected and the light source device to move relatively to each other for scanning the irradiated light on the surface of the object to be inspected; a polarized light separating device for separating polarized light disposed at a position in a dark field where scattered light irradiated onto and scattered from the object to be inspected is received; light-receiving device having a P-polarized light-receiving section and a S-polarized light-receiving section that separately detect P-polarized component light and S-polarized component light separated by the polarized light separating device; a control unit for controlling operation that includes application of stress by the stress applying means and relative motion of the light source device and the object to be inspected by the scanning driving unit; and a processing unit for performing processing operation of detecting defects and/or determining types of defects in the object to be inspected by comparing the intensities of P-polarized component light and S-polarized component light as detected by the light-receiving device and a polarization direction thereof obtained as a ratio of the intensities, in a state where stress is applied to the object to be inspected and in a state where no stress is applied to the object to be inspected, respectively with a predetermined threshold value.

In another aspect, the polarized light separating device is a beam displacer and the light-receiving device is a CCD imaging device that causes images by the P-polarized component light and S-polarized component light separated by the beam displacer to be formed on a CCD.

In still another aspect, the polarized light separating device is a polarization beam splitter and the light-receiving device comprises CCD imaging devices on which images by the P-polarized component light and S-polarized component light separated by the polarization beam splitter are formed individually.

In still another aspect, the support portion of the object to be inspected comprises a vacuum chuck and a piezoelectric element disposed on the top side of the vacuum chuck so that stress is applied to the object to be inspected through a deforming action exerted by the piezoelectric element in a state where the object to be inspected, placed on the piezoelectric element, is subjected to a suctioning action by the vacuum chuck.

In still another aspect, the support portion of the object to be inspected is formed as a heating stage and/or a cooling stage so that stress is applied to the object to be inspected, placed on the heating stage and/or cooling stage, through generation of thermal stress in the object to be inspected by heating and/or cooling thereof.

In still another aspect, the light source device generates infrared light and an internal cavity defect is detected in a silicon wafer for manufacturing semiconductor device as the object to be inspected.

In defect inspection of an object to be inspected according to the present invention, a polarized laser beam is irradiated onto the surface of an object to be inspected, P-polarized component light and S-polarized component light of the resulting scattered light are measured simultaneously and are compared between a state where stress is applied and a state where stress is not applied. As a result, defects can be detected in the object to be inspected and defects, such as internal deposits or cavity defects, foreign matter or scratches on the surface, or cracks in the surface layer, can be detected with high precision. Further, the defects can be classified by identifying the type thereof.

BRIEF DESCRIPTION OF THE DRAWINGS

FIG. 7 is a diagram illustrating an example of polarization direction during application of stress to an object to be inspected, in which

FIG. 12 is a diagram illustrating an example of stress applying means in the defect inspecting apparatus shown in FIG. 11, in which

DETAILED DESCRIPTION OF THE PREFERRED EMBODIMENTS

In the present invention, defects are inspected through irradiating light onto the surface of an object to be inspected having high homogeneity, the light being of a wavelength capable of penetrating into the object to be inspected and through measuring and analyzing the scattered light of the irradiated light. Examples of the object to be inspected include, for instance, wafers for manufacturing semiconductor circuit, such as ICs or the like; substrates for manufacturing optical functional element, such as diffraction gratings; superlattice structures; MEMS structures; as well as glass for liquid crystal panels and reticles. High homogeneity is a major issue in all of the foregoing.

Figure 1:
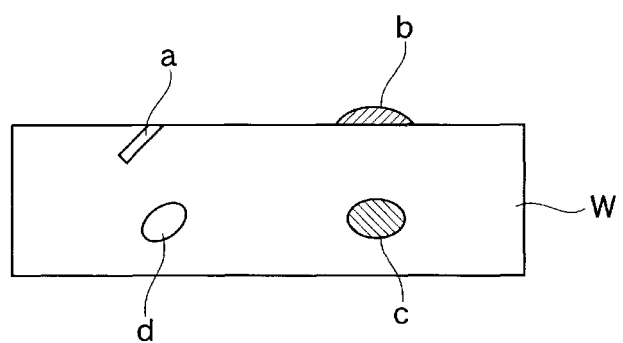
FIG. 1 is a diagram illustrating an example of defects in an object to be inspected.

As illustrated in FIG. 1, defects that impair the functionality of the object to be inspected include, for instance, cracks a in the surface layer, foreign matter (top contamination) and scratches b on the surface, internal deposits c, cavity defects d or the like. The functionality of articles such as semiconductor circuits or optical functional elements manufactured using materials containing such defects can be impaired on account of the defects. Therefore, it is necessary to inspect the products and to determine beforehand whether the defects can be repaired or the article cannot be used.

In the present invention, the light irradiated onto the object to be inspected is of a wavelength capable of penetrating into the object to be inspected. For instance, beam-like light from a laser or light obtained through decomposition of light from a halogen lamp is used. A case will be explained here in which a laser is used. The object to be inspected has a high degree of homogeneity, as described above. A silicon wafer for manufacturing semiconductor circuit will be explained here as a typical example.

Polarized light, obtained through polarization, by a polarizer, of a laser beam having a wavelength capable of penetrating into the object to be inspected, is irradiated obliquely onto the surface of the wafer and the resulting scattered light is detected by a light detection means disposed in a dark field. The above scattered light is detected both in a state where stress is applied to the wafer and in a state where stress is not applied to the wafer. The detection results are analyzed to detect and classify thereby the defects. Other than linearly polarized light, the light polarized by the polarizer may also be elliptically polarized light.

As is known, when cavity defects are present inside the crystal of a wafer, scattered light derived from defects in the crystal preserves the polarization direction of the incident light, in a state where stress is not applied to the wafer. However, the polarization state changes when the object to be inspected is in a stressed state.

As further considered of the dissimilar polarization state of the scattered light depending on whether stress is applied to the wafer or not, the elastic moduli of cavities and silicon are significantly different from each other in internal cavity defects (COP) in the crystal. As a result, application of stress gives rise to elastic strain in the vicinity of the cavities. Internal cavity defects in the crystal are ordinarily octahedral and stress concentrates, in particular, in the vicinity of the corners of the cavities. The strain field in the crystal structure in the vicinity of such local cavities causes the scattered light to contain scattered waves that are polarized in a direction that does not occur in ordinary scattering, i.e. the action of stress in internal cavity defects in the crystal gives rise to a photoelastic effect whereby the polarization state of scattered light varies with respect to that of incident light. As a result, the state of the detected scattered light resulting from internal cavity defects in the crystal is different depending on whether stress is being applied or not.

Cracks on the surface layer of a wafer, or on the insulator film (oxide film) formed on the wafer, exhibit also a photoelastic effect through concentration of stress at the tips of the cracks. As a result, the polarization direction varies depending on whether stress is applied, as in the case of cavities.

In case of foreign matter on the surface of the object to be inspected, it has been known that the change in the polarization state takes place upon scattering, unlike in the case of internal cavity defects. However, foreign matter on the surface is surrounded by vacuum or gas, hence the photoelastic effect upon application of stress is weak. Thus, the polarization state does not vary particularly depending on whether stress is being applied.

For deposits inside the object to be inspected, it has been checked experimentally whether the polarization direction of scattered light is identical to that of incident light, in the same way as in cavity defects. However, the elastic constant of deposits is ordinarily large, hence stress derived from the strain field is small and the photoelastic effect is weak.

Figure 2:
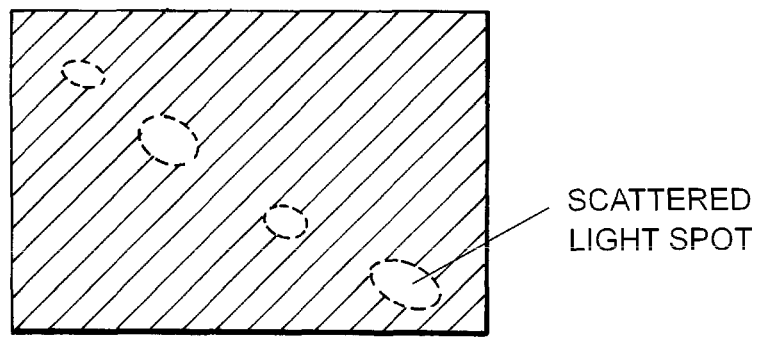
FIG. 2 is a diagram illustrating schematically an example of an image-formation pattern of scattered light caused by defects upon irradiation of a laser beam onto the surface of an object to be inspected.

No scattered light is generated at defect-free sites upon irradiation of a laser beam onto the wafer surface and therefore no scattered light is detected by a two-dimensional light detection means disposed in a dark field. At sites with defects, scattered light is detected by the two-dimensional light detection means. The scattered light is detected in the form of an image wherein bright spots from scattered light are dispersed in a black background, for instance as illustrated in FIG. 2.

Figure 3:
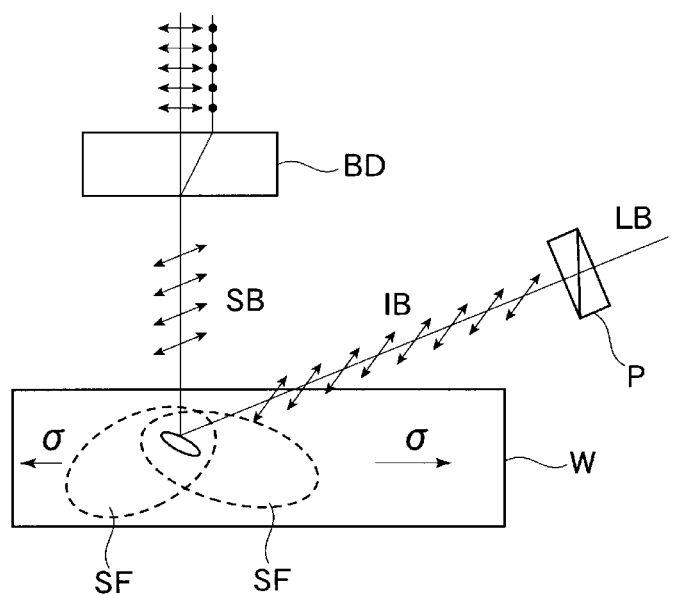
FIG. 3 is a diagram illustrating schematically the principle of inspection of an object to be inspected according to the present invention.

FIG. 3 is a diagram illustrating schematically the principles of inspection of an object to be inspected according to the present invention, wherein defects are detected and classified according to the type of defect. Herein a property is utilized with which a polarized laser beam, having impinged on a wafer W as an object to be inspected, is scattered by defects, so that the features of the scattering as well as changes in the polarization direction vary depending on the type of the defects. A laser beam LB, which have a wavelength capable of penetrating into the wafer W, is polarized by a polarizer P and is obliquely irradiated, as an incident beam IB, onto the surface of the wafer W. A scattered laser beam SB, scattered by defects D on the surface, in the surface layer or the interior of the wafer W, is separated in respect of polarization by a beam displacer BD disposed in a dark field. Herein, the reference symbol SF denotes the presence of a stress field around a defect in the wafer when the latter is under stress.

Figure 4:
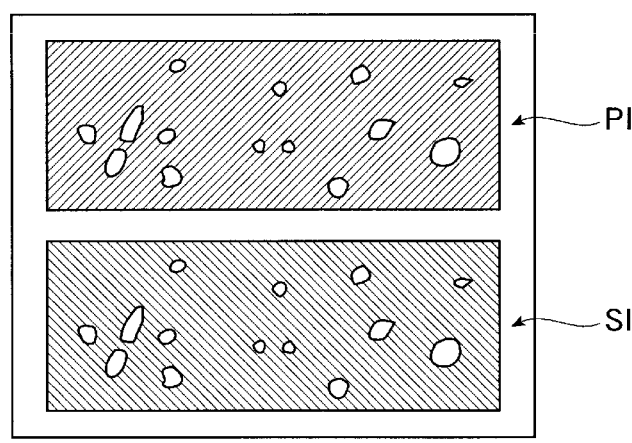
FIG. 4 is a diagram illustrating an example of images formed, on one plane, by dissimilar polarization components of light separated by a beam displacer shown in FIG. 3.

In a case where a calcite beam displacer BD is used, a P-polarized component beam and an S-polarized component beam are separated by about 2 mm (depending on the length of the calcite). When captured by a CCD camera, the beams are imaged in the form of separate images, namely an image (PI) of the P-polarized component light and an image (SI) of the S-polarized component light, as illustrated in FIG. 4. For identical defects, the distribution images (PI, SI) of bright points from scattered light exhibit a similar bright point distribution pattern. However, the characteristics of the respective bright points, such as brightness, are dissimilar between bright points of the P-polarized component light and those of the S-polarized component light.

Accordingly, values are obtained, which characterize the bright points in the image (PI) of the P-polarized component light and bright points in the image (SI) of the S-polarized component light respectively, and then the ratio between the values of both components is worked out. The integrated intensity value of the bright points is obtained, as the above characterizing value, for each image. The integrated intensity value of the bright points results from integrating the brightness values of pixels in an area, which includes the periphery of the bright points, the integration being made for the area. To define the above area, the position of a brightness peak site and the position of an intermediate brightness value, which is the average of the brightness value at the peak site and a background brightness value, are obtained and then a square, the center of which stands at the peak site position and the sides of which are twice the distance from the peak site to the position of the intermediate brightness value, is taken as the area of brightness integration.

The integrated intensity value of each bright point in the image (PI) is obtained and the data on the position and the integrated intensity value of the bright point are stored. Likewise, the integrated intensity value of each bright point in the image (SI) is obtained and the data on the position and the integrated intensity value of the bright point are stored. The operation of acquiring and storing data on the scattered light intensity (integrated intensity value) at positions, where scattered light is generated upon irradiation of a laser beam onto the wafer surface, and data on the positions, at which bright points are present, is performed in a state where stress is not applied to the wafer and in a state where stress is applied to the wafer respectively.

Next, the polarization directions of scattered light, at a same position of the object to be inspected, in a state where no stress is acting and in a state where stress is acting are compared to work out a polarization direction difference and it is determined whether that difference exceeds a threshold value or not. This constitutes a benchmark for defect type determination. Elliptically polarized light may also be used as the polarized light in the present invention, besides linearly polarized light. In the case of elliptically polarized light, the long axis direction thereof is the polarization direction.

Figure 5:
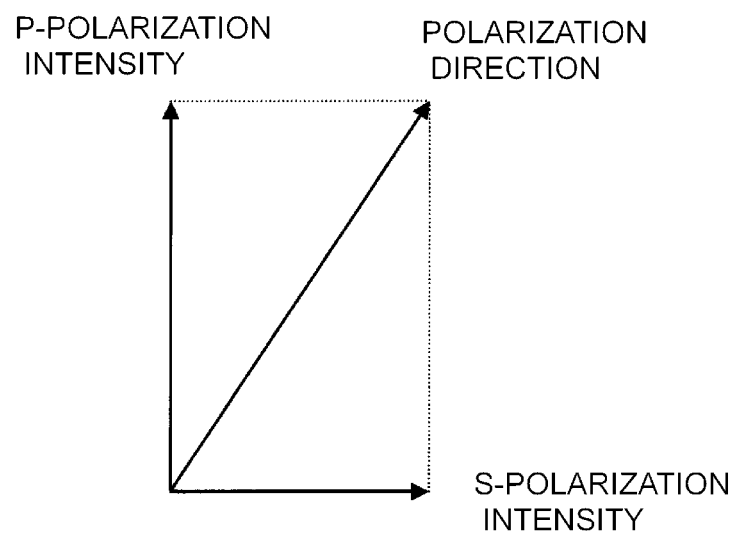
FIG. 5 is a diagram illustrating a relationship between component light intensities and polarization direction.

The polarization direction of scattered light is obtained on the basis of the polarized light intensity represented by the integrated intensity values obtained for each bright point, as illustrated in FIG. 5. In FIG. 5, the P-polarization intensity is the polarized light intensity for a bright point of those in the image (PI) and the S-polarization intensity is the polarized light intensity for a bright point corresponding to the image (SI). The ratio between P-polarization intensity and S-polarization intensity, which corresponds to a tangent function, represents the polarization direction. The polarization direction is thus defined to be a magnitude obtained as the ratio between P-polarization intensity and S-polarization intensity. The polarization direction is obtained also for the incident light.

Figure 6A:
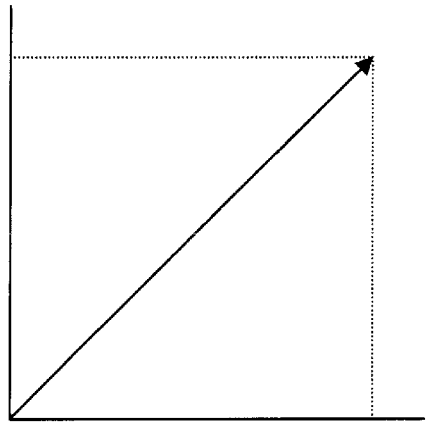
FIG. 6(a) is a diagram illustrating an example of polarization direction of incident light and FIG. 6(b) is a diagram illustrating an example of polarization direction of light scattered by defects.
Figure 6B:
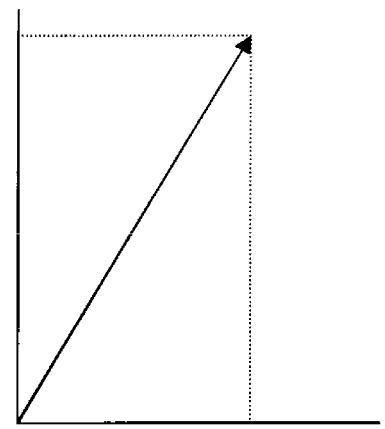

FIG. 6(a) illustrates an example of the polarization direction of incident light and FIG. 6(b) illustrates an example of the polarization direction of such scattered light that incident light having the polarization direction of FIG. 6(a) has been scattered by defects in the wafer. The polarization direction of the scattered light varies depending on the scattering entities (defects) and ordinarily deviates somewhat from the polarization direction of incident light.

Figure 7A:
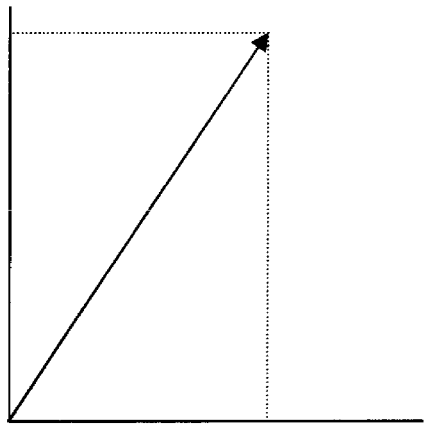
FIG. 7(a) illustrates an instance where defects are absent and FIG. 7(b) illustrates an instance where defects are present.
Figure 7B:
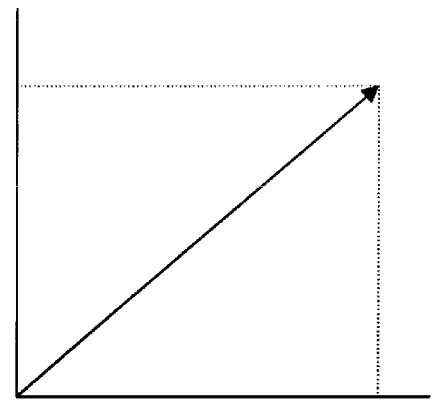

FIGS. 7(a), 7(b) illustrate comparatively an instance where cracks and/or cavity defects are absent and an instance where the foregoing are present respectively. FIG. 7(a) illustrates an instance where no cracks or cavity defects are present and the polarization direction does not change upon application of stress. In a case where cracks and/or cavity defects are present, the polarization direction changes through application of stress, as illustrated in FIG. 7(b).

When the difference in the polarization directions of scattered light between a state in which stress is applied and a state where no stress is applied is large enough to exceed a given threshold value, the scattered light is deemed to arise from cracks or from internal cavity defects in the crystal; when the difference in the polarization directions of scattered light between a state in which stress is applied and a state where no stress is applied is smaller than a given threshold value and does not vary much, the scattered light is deemed to arise from surface foreign matter or from deposits. In such a manner, defects are classified on the basis of detection results of the scattered light. The threshold values, which vary depending on the type of object to be inspected, such as a wafer, and on the nature of the defects, are obtained beforehand in accordance with, for instance, the types of the objects to be inspected.

Types of defects can be classified according to the presence or absence of changes in the polarization direction and to the intensity of polarized light. Classification is summarized in such a form as Table 1.

TABLE 1

| | Without stress application | | With stress application | | |
|---|---|---|---|---|---|
| Defect types | S-polarized light | P-polarized light | S-polarized light | P-polarized light | Polarization direction |
| Internal deposits | Strong | Very weak | Small change | Small change | x at or below threshold value |
| Cavity defects | Strong | Very weak | Change | Change | o at or above threshold value |
| Surface foreign matter | Strong | Strong | Small change | Small change | x at or below threshold value |
| Cracks | Weak | Very weak | Change | Change | o at or above threshold value |

In Table 1, the polarization direction of incident light is S-polarization. That is because an S-polarized component is ordinarily used for observing internal defects. The changes in the polarization direction due to the various defects are explained next.

Internal Deposits

It is confirmed experimentally that the polarization direction of incident light is conserved in scattered light for internal deposits. In the absence of applied stress, the light is scattered as-is and the polarization direction does not change. The scattered light intensity changes upon generation of a stress field around foreign matter through application of stress. However, the effect is small and the change in the polarization direction is no greater than a threshold value.

Cavity Defects

Similarly to internal deposits, the polarization direction of scattered light is conserved in the case of internal cavity defects. Accordingly, in the absence of applied stress, scattered light behaves in the same way as in the case of internal deposits. Both the P-polarized component and the S-polarized component change upon generation of a stress field around cavity defects through application of stress. The polarization direction changes also as a result.

Surface Foreign Matter or Scratches

Surface foreign matter does not preserve the polarization direction, due to depolarization effects. Therefore, a strong S-polarized component is observed even upon incidence of P-polarized light. If the polarization direction of incident light and the polarization direction of scattered light are significantly dissimilar in the absence of applied stress, it is determined at that point in time that the defect is surface foreign matter. (Even under applied stress, only a very weak stress field is ordinarily present around surface foreign matter, hence the polarization direction does not change.)

Cracks

Cracks are defects that reach from the surface to the interior and can be thought of as identical to cavity defects. The radius of curvature at the tip of the crack is extremely small. Therefore, greater stress than in the case of cavity defects concentrates at the tips of cracks and the change in polarization direction is greater than that in cavity defects.

Figure 8A:
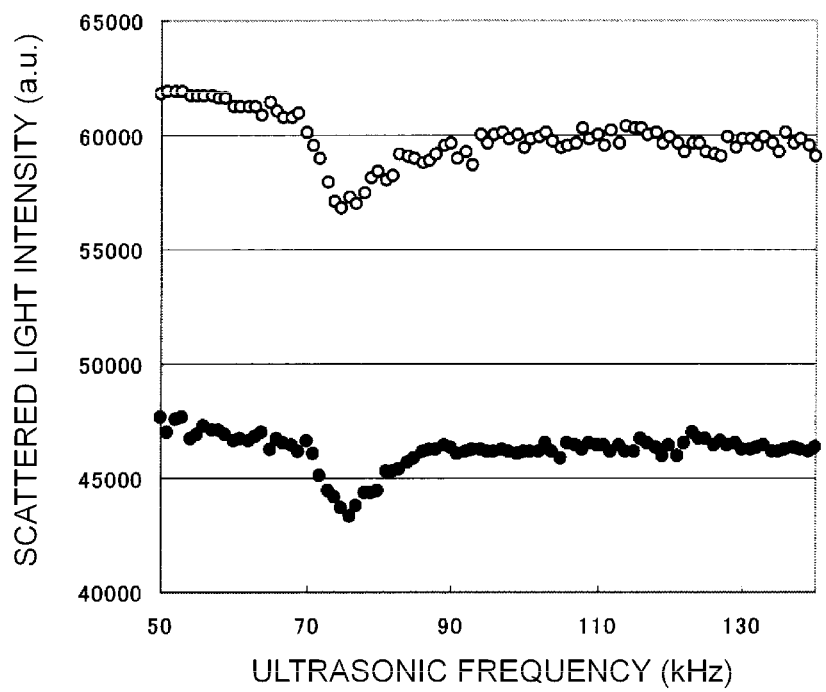
FIG. 8(a) is a graph illustrating changes of intensity of light scattered by defects, depending on ultrasonic frequency, at a time when ultrasonic waves, as a stress applying means, are not applied
Figure 8B:
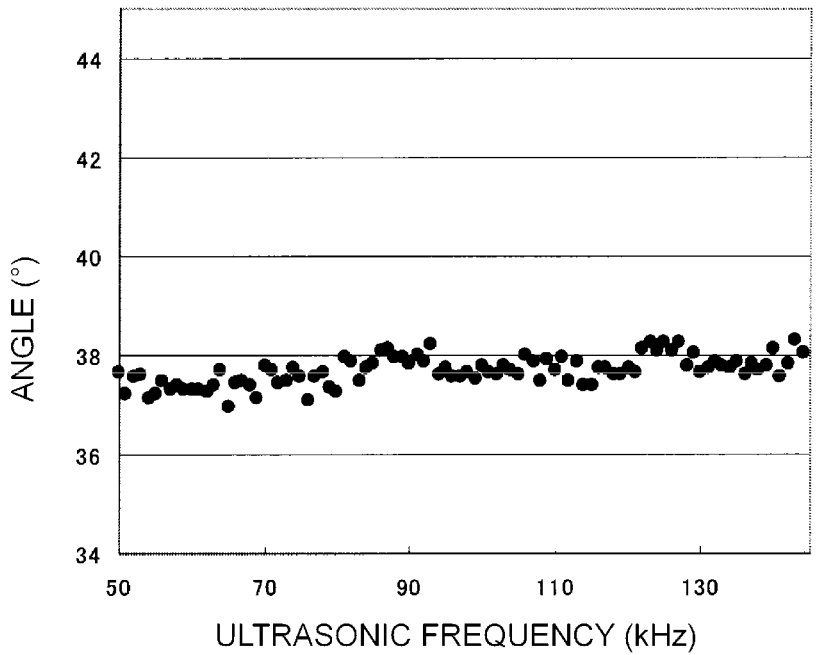
FIG. 8(b) is a graph illustrating the change of polarization direction, determined on the basis of a ratio between the intensities of both polarization components, depending on ultrasonic frequency.

FIG. 8 and FIG. 9 illustrate the results of measurements of polarized light component intensity in a case where an ultrasonic wave generation means is used as a stress applying means. FIG. 8(a) illustrates the change in intensity of P-polarized light and S-polarized light of scattered light depending on ultrasonic frequency in the situation where no ultrasonic waves act on a silicon wafer as the object to be inspected, wherein ● denotes P-polarized light and ○ denotes S-polarized light. FIG. 8(b) illustrates the polarization direction obtained on the basis of the ratio between the P-polarized light intensity and the S-polarized light intensity. The polarization direction exhibits thus a substantially constant value when no ultrasonic waves are acting.

Figure 9A:
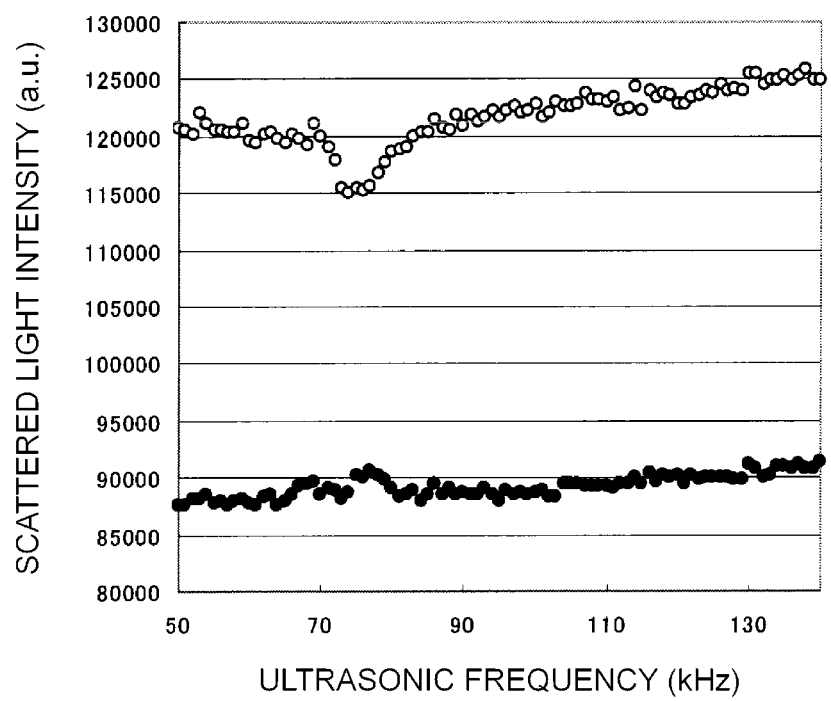
FIG. 9(a) is a graph illustrating changes of intensity of light scattered by defects, depending on ultrasonic frequency, at a time when ultrasonic waves, as a stress applying means, are applied
Figure 9B:
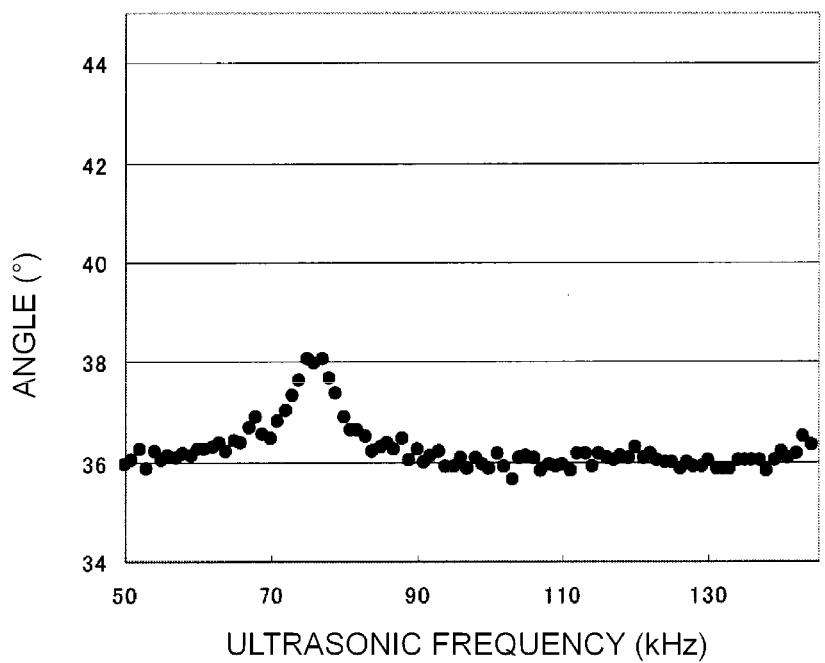
FIG. 9(b) is a graph illustrating the change of polarization direction, determined on the basis of a ratio between the intensities of both polarization components, depending on ultrasonic frequency.

FIG. 9(a) illustrates the change in intensity of P-polarized light and S-polarized light of scattered light depending on ultrasonic frequency in the situation where ultrasonic waves act on the silicon wafer, wherein ● denotes P-polarized light and ○ denotes S-polarized light. FIG. 9(b) illustrates the polarization direction obtained on the basis of the ratio between the P-polarized light intensity and the S-polarized light intensity. When ultrasonic waves are acting, the polarization direction changes on the whole. In particular, the polarization direction changes by about 2° when the ultrasonic frequency is about 70 kHz.

Thus, defects in the object to be inspected are detected on the basis of the polarized light component intensity of scattered light during application of stress and during absence of applied stress, as in FIG. 8 and FIG. 9, and the type of the defect is determined by referring to Table 1.

The length, by which light irradiated onto the object to be inspected penetrates from the surface, varies depending on the wavelength of the light. The type and wavelength of irradiation light is selected in accordance with conditions that include, for instance, the material of the object to be inspected and the approximate depth from the surface that is to be observed. In the case of wafers for manufacturing semiconductor circuits, the penetration depth from the surface is of several microns for visible-light laser. By contrast, infrared laser pervades the interior of the wafer, hence is suitable for detecting cavity defects inside the wafer. The oxide film formed on the wafer is transparent for visible light. Thus cracks and cavity defects in the film can also be detected.

To apply stress to an object to be inspected such as a wafer or the like, the object to be inspected may be subjected to any kind of deformation, which may involve, for instance, placing the inspection object on a vacuum chuck and subjecting the inspection object to a suctioning action, imparting a suctioning action by way of a piezoelectric element, imparting a heating action, subjecting the object to be inspected to the action of ultrasonic waves, to the application of a static load by a weight or a load using a pressing means. These will be explained specifically relating to a defect inspecting apparatus equipped with such means for imparting deformation to the object to be inspected.

Figure 10:
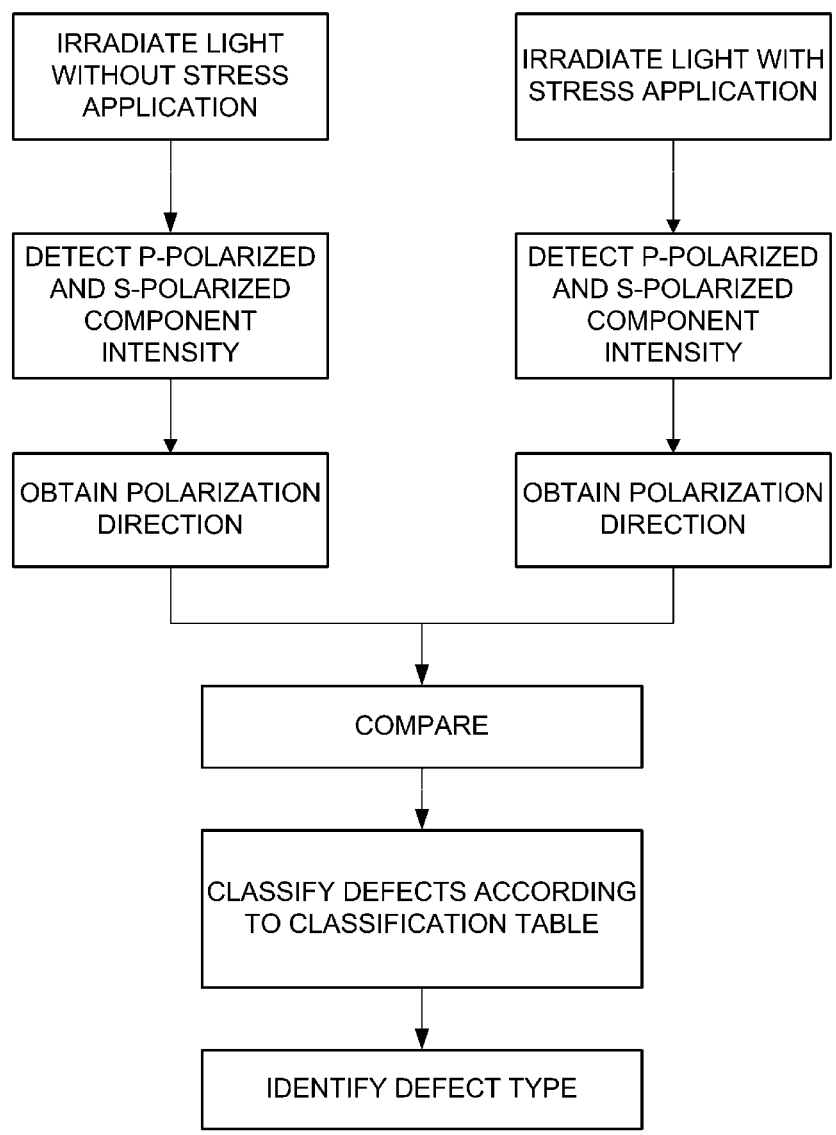
FIG. 10 is a flow diagram of a method for inspecting defects of an object to be inspected according to the present invention.

FIG. 10 illustrates a process flow of detection of defects in an object to be inspected.

<Defect Detection Apparatus>

One embodiment of the defect inspecting apparatus for inspecting an object to be inspected according to the present invention will be explained with reference to FIG. 11. The explanation will focus on an instance where the object to be inspected is a silicon wafer for manufacturing semiconductor circuits and laser light is used as the irradiation light.

Figure 11:
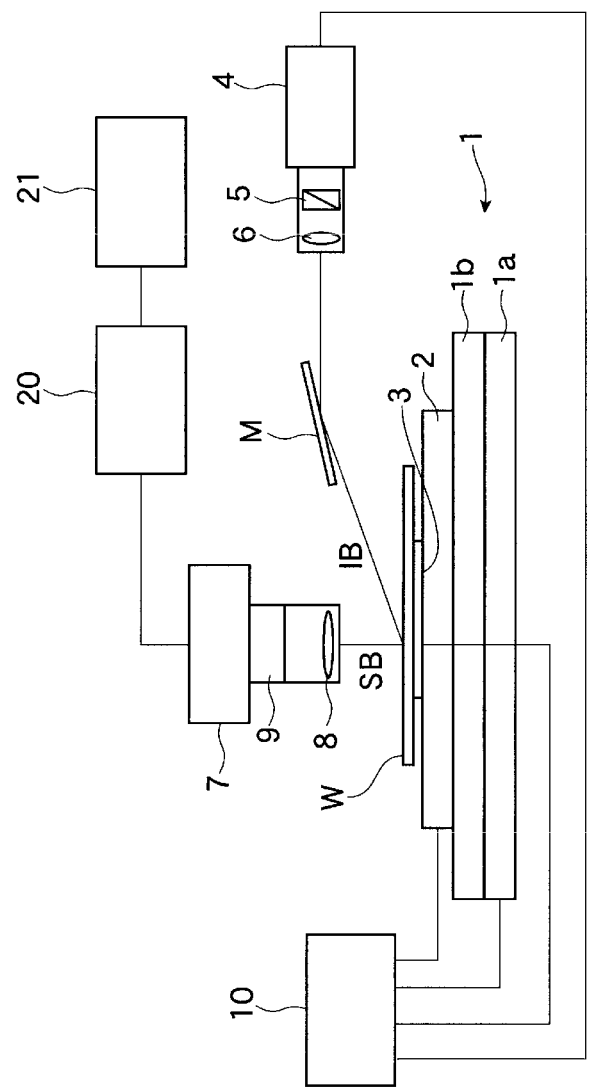
FIG. 11 is a diagram illustrating an example of the configuration of a defect inspecting apparatus according to the present invention.

In FIG. 11, the reference numeral 1 denotes an XY stage that comprises a base 1a and a bedplate 1b which is placed on the base 1a and can be driven in the XY directions. The reference numeral 2 denotes a fixing device for a wafer which is secured onto the bedplate 1b of the XY stage 1 and mounts a wafer W. In the present example, a vacuum chuck is used as the fixing device for the wafer. The reference numeral 3 denotes a plate-like piezoelectric element, on which the wafer W is placed. The vacuum chuck, as the securing device 2 for a wafer, and the piezoelectric element 3 make up means for applying stress to the wafer, in that the wafer W is subjected to bending deformation through suctioning by the vacuum chuck and through the action of the piezoelectric element.

The reference numeral 4 denotes a laser device. The laser used has a wavelength capable of penetrating into a silicon wafer, for instance a wavelength of 375 nm. The reference numeral 5 denotes a polarizer that polarizes the laser; the reference numeral 6 denotes a condensing lens and M denotes a reflecting mirror. The reference numeral 7 denotes a CCD imaging device which is disposed at a dark field position and receives scattered light SB that results from scattering of an incident beam (IB), which is polarized by the polarizer 5 and incident obliquely on the surface of the wafer W, upon its incidence; the reference numeral 8 denotes an objective lens of the CCD imaging device; and the reference numeral 9 denotes a beam displacer that polarizes and separates light that passes through the objective lens.

The reference numeral 10 denotes a driving control unit that performs displacement control of the wafer W in the XY direction by way of the XY stage 1, control of the suction operation of the vacuum chuck as the fixing device 2 a wafer, control of the operation of the piezoelectric element and control of the operation of the laser device. The reference numeral 20 denotes an image analyzing/processing device for carrying out a computing process of image data from scattered light, as captured by the CCD imaging device, and is provided with a storage means necessary for image analysis and processing. The reference numeral 21 denotes a display for displaying, for instance, images obtained by the CCD imaging device, as well as results of the analysis and processing.

Figure 12A:
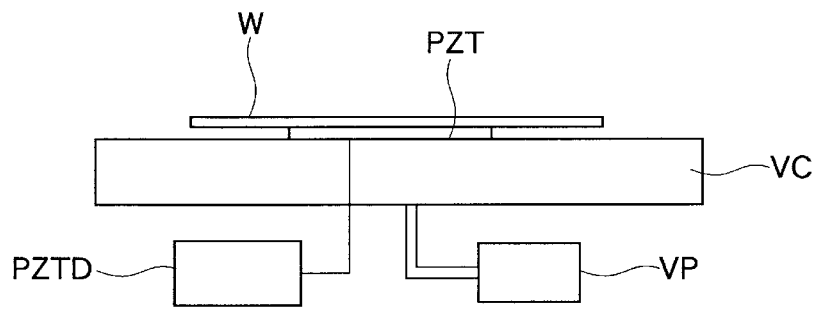
FIG. 12(a) illustrates a configuration where the stress applying means comprises a vacuum chuck and a piezoelectric element.
Figure 12B:
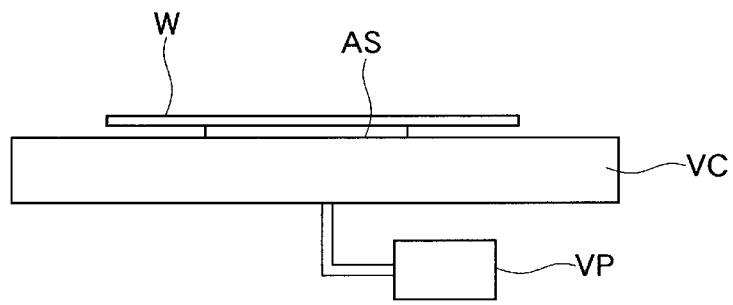
FIG. 12(b) illustrates a configuration where the stress applying means comprises a vacuum chuck and FIG. 12(c) illustrates a configuration where the stress applying means comprises a heating means.
Figure 12C:
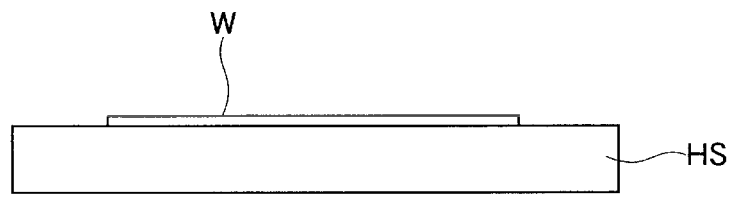

FIGS. 12(a) to 12(c) illustrate examples of the wafer fixing device 2 and arrangement of the stress applying means, wherein FIG. 12(a) illustrates a combination of a piezoelectric element and the vacuum chuck shown in FIG. 11. Through the suctioning action of a vacuum pump VP, the vacuum chuck VC, as the wafer fixing means, exerts a suction action on the placed wafer W, via the piezoelectric element. The piezoelectric element PZT, which is operated with voltage applied by a piezoelectric element driving unit PZTD, exerts a deforming action on the wafer W, whereby stress is applied to the wafer W.

FIG. 12(b) illustrates an instance of application of stress to the wafer W only through the action of the vacuum chuck VC. In this case, the piezoelectric element such as the one in FIG. 12(a) is omitted and instead a height adjusting member AS having a thickness equivalent to that of the piezoelectric element is provided. The wafer W is placed on the height adjusting member AS and the wafer W is subjected to deformation and stress application through the action of the vacuum chuck VC.

FIG. 12(c) illustrates an instance of application of stress onto the wafer W by way of a heating device HS. In a case where the object to be inspected is a wafer for manufacturing semiconductor circuits comprising a silicon layer with a silicon oxide coating layer, stress is generated through uneven deformation brought about by heating, since in this case the wafer is not a medium having a homogeneous coefficient of thermal expansion throughout the medium. Some stress concentrates around defects such as cracks or the like also in the case of overall thermal expansion of a wafer comprising a single material.

Thus, heating gives rise to internal stress if the material of the object to be inspected exhibits some non-homogeneity. Even when the material of the object to be inspected is deemed to be homogeneous, internal stress can still be generated in the inspection object depending on the way in which heating is performed. The way in which heating is carried out may involve dividing the area of the object to be inspected that is to be heated into a plurality of regions, providing heating means or cooling means that yield a different amount of heating at each region and performing heating or cooling, to elicit thereby a non-homogeneous heating state in the object to be inspected and allow stress to be generated in the interior of the object to be inspected. For instance, heating means may heat one face of the object to be inspected while cooling means cools the other face, whereby stress can be generated in the interior due to the difference between thermal expansion at a top face and one at a lower face.

Various other conceivable means for applying stress to the object to be inspected may involve, besides the above-described ones, downwards suction of the object to be inspected while the central area of the latter is held up; or impartment of a pushing load to the object to be inspected from below with the tip of a pushing rod at its central area while placing a weight on its periphery. Other suitable methods for imparting stress to the object to be inspected may involve application of a tensile, torsional, shear or bending load by way of a fixture. Further, stress can be applied through the action of ultrasonic waves on the object to be inspected by providing an ultrasonic wave generating means in the fixing means of an object to be inspected. Although the action of ultrasonic waves does not give rise to macro-level deformation of the object to be inspected, it is found that the oscillating action of the ultrasonic waves imparts micro-level stress. The stress applying means can be thus appropriately selected in accordance with the type, dimensions and conditions of the object to be inspected of interest.

The present invention can be used for evaluating the quality of an object to be inspected and to determine ways of removing defects, through detection of defects and classification of defect types in an object to be inspected that are made up of a material having high homogeneity, for instance wafers for manufacturing semiconductor circuits such as ICs or the like; substrates for manufacturing optical functional elements such as diffraction gratings; superlattice structures; MEMS structures; glass for liquid crystal panels; or reticles.

What is claimed is:

1. A method for inspecting defects in an object to be inspected by polarizing, with a polarizer, light of a wavelength that can penetrate into the object to be inspected and irradiating the polarized light onto a surface of the object to be inspected, thereby detecting scattered light therefrom in a state where stress is not applied to the object to be inspected and in a state where stress is applied thereto, the method comprising:
    irradiating polarized light obliquely onto the surface of the object to be inspected, at a position thereof, in a state where stress is not applied to the object to be inspected and separating scattered light generated as a result of the irradiation into P-polarized component light and S-polarized component light, then obtaining intensities of each component light and a polarization direction as a ratio thereof;
    irradiating polarized light obliquely onto the surface of the object to be inspected, in a state where stress is applied to the object to be inspected, at the same position of the surface as where the light was irradiated in a state where no stress is applied to the object to be inspected and separating scattered light generated as a result of the irradiation into P-polarized component light and S-polarized component light, then obtaining intensities of each component light and a polarization direction as a ratio thereof; and
    detecting defects and/or classifying the defects by comparing the intensity and polarization direction of each component light obtained in a state where no stress is applied to the object to be inspected and the intensity and polarization direction of each component light obtained in a state where stress is applied to the object to be inspected respectively with a predetermined threshold value.

2. The method for inspecting defects according to claim 1, wherein the scattered light from light irradiated at the position on the surface of the object to be inspected is separated, by means for separating polarized light disposed in a dark field, into a P-polarized polarization component and an S-polarized polarization component so as to obtain the intensity of each component light.

3. The method for inspecting defects according to claim 1, wherein a defect in the object to be inspected is determined to be a crack or a cavity defect when a difference between the polarization direction of scattered light obtained in a state where no stress is applied to the object to be inspected and the polarization direction of scattered light obtained in a state where stress is applied to the object to be inspected exceeds a predetermined threshold value and a defect in the object to be inspected is determined to be another type of defect when the difference does not exceed the predetermined threshold value.

4. The method for inspecting defects according to claim 1, wherein the object to be inspected is disposed on a vacuum chuck with a piezoelectric element interposed therebetween and stress is applied to the object to be inspected through a suctioning action exerted by the vacuum chuck on the object to be inspected and through an action exerted by the piezoelectric element.

5. The method for inspecting defects according to claim 1, wherein the object to be inspected is heated and/or cooled so as to generate thermal stress in a state where the object to be inspected is disposed on a heating stage, whereby the object to be inspected is subjected to stress.

6. The method for inspecting defects according to claim 1, wherein the object to be inspected is subjected to stress through the action of ultrasonic waves on the object to be inspected.

7. The method for inspecting defects according to claim 1, wherein the object to be inspected is a silicon wafer for manufacturing semiconductor devices and an internal cavity defect is detected using infrared light as the irradiated light.

8. A defect inspecting apparatus, comprising: a support portion for supporting an object to be placed thereon;
   stress applying means for applying stress to the object to be inspected that is capable of switching between a state in which stress is applied to the object to be inspected placed on the support portion and a state in which no stress is applied;
   a light source device that irradiates light with a wavelength that can penetrate into the object to be inspected via a polarizer obliquely onto a surface of the object to be inspected supported by the support portion;
   a scanning driving unit that causes the object to be inspected and the light source device to move relatively to each other for scanning the irradiated light on the surface of the object to be inspected;
   a polarized light separating device for separating polarized light disposed at a position in a dark field where scattered light irradiated onto and scattered from the object to be inspected is received;
   a light-receiving device having a P-polarized light-receiving section and a S-polarized light-receiving section that separately detect P-polarized component light and S-polarized component light separated by the polarized light separating device;
   a control unit for controlling operation that includes application of stress by the stress applying means and relative motion of the light source device and the object to be inspected by the scanning driving unit; and
   a processing unit for performing processing operation of detecting defects and/or determining types of defects in the object to be inspected by comparing the intensities of P-polarized component light and S-polarized component light as detected by the light-receiving device and a polarization direction thereof obtained as a ratio of the intensities, in a state where stress is applied to the object to be inspected and in a state where no stress is applied to the object to be inspected, respectively with a predetermined threshold value.

9. The defect inspecting apparatus according to claim 8, wherein polarized light separating device is a beam displacer and the light-receiving device is a CCD imaging device that causes images by the P-polarized component light and S-polarized component light separated by the beam displacer to be formed on a CCD.

10. The defect inspecting apparatus according to claim 8, wherein the polarized light separating device is a polarization beam splitter and the light-receiving device comprises CCD imaging devices on which images by the P-polarized component light and S-polarized component light separated by the polarization beam splitter are formed individually.

11. The defect inspecting apparatus according to claim 8, wherein the support portion of the object to be inspected comprises a vacuum chuck and a piezoelectric element disposed on the top side of the vacuum chuck so that stress is applied to the object to be inspected through a deforming action exerted by the piezoelectric element in a state where the object to be inspected, placed on the piezoelectric element, is subjected to a suctioning action by the vacuum chuck.

12. The defect inspecting apparatus according to claim 8, wherein the support portion of the object to be inspected is formed as a heating stage and/or a cooling stage so that stress is applied to the object to be inspected, placed on the heating stage and/or cooling stage, through generation of thermal stress in the object to be inspected by heating and/or cooling thereof.

13. The defect inspecting apparatus according to claim 8, wherein the light source device generates infrared light and an internal cavity defect is detected in a silicon wafer for manufacturing semiconductor device as the object to be inspected.

\* \* \* \* \*